United States Patent [19]

Krone et al.

[11] Patent Number: 5,505,784
[45] Date of Patent: Apr. 9, 1996

[54] POLYCONDENSATES WHICH CONTAIN TARTARIC ACID DERIVATIVES, PROCESSES FOR THEIR PREPARATION AND USE THEREOF

[75] Inventors: Volker Krone, Hofheim am Taunus; Michael Magerstädt, Egelsbach; Axel Walch; Günter Ditzinger, both of Frankfurt am Main; Norbert Lill, Kronberg/Ts. all of Germany

[73] Assignee: Hoechst Aktiengesellschaft, Frankfurt am Main, Germany

[21] Appl. No.: 370,885

[22] Filed: Jan. 10, 1995

Related U.S. Application Data

[62] Division of Ser. No. 886,197, May 21, 1992, Pat. No. 5,391,696.

[30] Foreign Application Priority Data

May 24, 1991 [DE] Germany .......................... 41 16 936.0

[51] Int. Cl.$^6$ ........................................................ A61B 8/14
[52] U.S. Cl. .................. 128/662.02; 128/653.1; 128/654; 128/660.01; 128/660.07; 128/660.02; 528/272; 528/288; 528/289; 528/290; 528/291; 528/294; 528/295; 528/298; 528/302; 528/306; 528/308; 528/308.6
[58] Field of Search ................... 128/653.1, 654, 128/660.01, 660.02, 660.07, 662.02; 528/272, 288, 289, 290, 291, 294, 295, 298, 302, 306, 308, 308.6

[56] References Cited

U.S. PATENT DOCUMENTS

| | | | |
|---|---|---|---|
| 3,297,033 | 6/1967 | Schmitt et al. . | |
| 3,608,063 | 9/1971 | Banker | 424/485 |
| 3,773,919 | 11/1974 | Boswell et al. . | |
| 4,093,709 | 6/1978 | Choi et al. | 424/19 |
| 4,138,344 | 2/1979 | Choi et al. | 252/1 |
| 4,180,646 | 12/1979 | Choi et al. | 528/153 |
| 5,084,553 | 1/1992 | Hess et al. | 528/361 |

FOREIGN PATENT DOCUMENTS

| | | |
|---|---|---|
| 635200 | 8/1989 | Australia . |
| 30351/89 | 3/1993 | Australia . |
| 0327490A1 | 2/1989 | European Pat. Off. . |
| 0426055A2 | 10/1990 | European Pat. Off. . |
| 1520194 | 11/1969 | Germany . |
| 1944694 | 5/1970 | Germany . |
| 52-078297 | 7/1977 | Japan . |
| 52-147697 | 12/1977 | Japan . |
| 89/000690 | 1/1989 | WIPO . |
| WO89/06978 | 8/1989 | WIPO . |

OTHER PUBLICATIONS

Ogata et al. Active Polycondensation of Methylene Tartarate With Hexamethylenediamine, Polymer Letters Edition, vol. 14, pp. 409–412 (1976).

CA 87 (24) 185254y.
CA 88 (26) 191775f.
Akelah, et al., Agricultural Polymers With a Combined Herbicide/Fertilizer Function–I. Tartrate–Based Systems, Eur. Polym. J. vol. 28. No. 5, pp. 453–463, 1992.
Chemical Abstracts, Band 91, Nr. 10, 1979, AN: 7525y;Abstract JP-A-54032594 Mitsubishi Gas Chemical Co., Sep. 3, 1979.
Search Report, European Patent Application EP 92 10 8251 dated Feb. 2, 1994 and Annex to Search Report.
Microbubbles Have Intracardiac Velocities Similar to Those of Red Blood Cells, R. Lecine et al., JACC, vol. 3, No. 1, Jan. 1984, pp. 28–33.
Relation Of in Vivo Blood Flow to Ultrasound Echogenicity, J. Machi et al. J. Clin. Ultrasound, vol. 11, Jan. 1983, pp. 3–9.
Syntheses of Polyamides and a Polyester Containing 2,6–Dichlorobenzaldehyde Schacht et al., Makromol, Chem, vol. 179, (1978) pp. 837–840.
Vollmert, Makromolekularen Chemie, vol. III, pp. 60–71 (1982).
M. Carmack et al., J. Org. Chem., 33 1668, pp. 2171–2173.
J. Moore et al. Macro Molecules, 11, No. 3, 1978, pp. 568–573.
P. Feit, J. Med. Chem., 7, 1964, pp. 14–17.

Primary Examiner—Samuel A. Acquah
Attorney, Agent, or Firm—Finnegan, Henderson, Farabow, Garrett & Dunner

[57] ABSTRACT

The invention relates to polycondensates which consist of at least 95 mol % of recurring structural units of the formula I

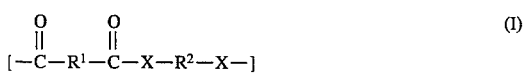

where $R^1$ is a 2,3-O-alkylidenetartaric acid derivative (II) or furo[2,5] (V), alkyl, alkenyl, cycloalkyl, cycloalkenyl, aryl or a heterocycle, X is —O—, —NH— or —S— and $R^2$ is 2,3-O-alkylidene-L-threitol (III) or a compound of the formula VI, alkyl, alkenyl, cycloalkyl, cycloalkenyl, aryl or a heterocycle, with the proviso that more than 5 mol % of the radicals $R^1$ and/or $R^2$ are present in the polycondensate of the formula I, where $R^1$ is compound of the formula II or $R^2$ is a compound of the formula III or $R^1$ is a compound of the formula II and $R^2$ is a compound of the formula III, or in which more than 5 mol % of the radicals $R^1$ and $R^2$ are present in the polycondensate of the formula I, where a) $R^1$ is a compound of the formula V and $R^2$ is a compound of the formula VI, or b) $R^1$ is phenyl[1,2], phenyl[1,3] or phenyl[1,4] and $R^2$ is a compound of the formula VI, to a process for the preparation of these polycondensates, and to their use for the production of depot preparations with controlled release of active substance or for the production of ultrasonic contrast agents.

27 Claims, No Drawings

POLYCONDENSATES WHICH CONTAIN TARTARIC ACID DERIVATIVES, PROCESSES FOR THEIR PREPARATION AND USE THEREOF

This is a division of application Ser. No. 07/886,197, filed May 21, 1992 now U.S. Pat. No. 5,391,696.

The invention relates to polycondensates which are distinguished by the presence of tartaric acid derivatives, to processes for their preparation and to the use thereof for depot preparations with controlled active substance release or for the preparation of ultrasonic contrast agents.

In particular for the administration of active substances, a modern pharmaceutical therapy requires novel administration forms which combine a controlled release rate of the active substances with high biocompatibility of the depot. Because of the increasing importance of chronic diseases and long term-orientated therapy concepts in human and veterinary medicine, a long-lasting controlled release of active substance is of great relevance. Matrix materials which are particularly advantageous for such depot systems are biodegradable polymers, as the bioerosion essentially controls the release of active substance and makes the surgical removal of a depot of this type unnecessary.

In biologically degradable pharmaceutical release systems, such as indicated in U.S. Pat. No. 4,093,709, the active substance is dispersed in a biodegradable polymer which releases the active substance on degradation. Typical biologically degradable polymers which have been investigated most according to the prior art are homo- and copolyesters, in particular of lactic and glycolic acid, such as are described in U.S. Pat. Nos. 3,773,919 and 3,297,033. Disadvantages are, inter alia, the poorly controllable swellability of the polyesters in physiological medium and the complex mechanism of active substance release associated with this. Additionally, in general after a considerable "initial burst" only a small to moderate release rate is effected.

Not only in therapy, but also in diagnosis, preparations containing polymers prove to be suitable more and more frequently. This is the case, for example, in ultrasonic diagnosis. Because of simple handling without complications, it has found very wide use in medicine. Ultrasonic waves are reflected at boundary surfaces of different tissue types. The echo signals formed in this way are electronically amplified and rendered visible.

The representation of blood vessels and internal organs by means of ultrasound in general does not allow the representation of the blood flow present in these. Liquids, in particular blood, only give ultrasonic contrast if density differences from the surroundings exist. Contrast agents used in medical ultrasonic diagnosis are, for example, substances containing gases or producing gases, as the impedance difference between gas and surrounding blood is substantially larger than that between liquids or solids and blood (Levine R. A., J Am Coll Cardiol 3:28, 1989; Machi I. J CU 11:3, 1983).

EP-A1-0,327,490 describes microparticles which consist of amyloses or synthetic biodegradable polymers and a gas and/or a liquid having a boiling point of less than 60° C. Disadvantages of these polymers are their tacky consistency in water or blood, their poor biogradability or the possibility that toxic degradation products can arise.

To date, the preparation of some very low molecular weight protected tartaric acid esters has been described (Schacht et al. Makromol Chem. 179, (1978), 837–840), which exhibit a viscosity of 0.04 dl.g$^{-1}$, measured in dimethylformamide at 25° C. The viscosities described show that they are not polymers of protected tartaric acid derivatives.

The object of the present invention is to find polycondensates which have a mechanically stable structure, can be easily suspended in water, have a low swelling power in water and do not have any greasy tacky consistency, which are easily degradable chemically or biologically to essentially non-toxic products and whose degradation products are water-soluble.

It has now been found that polycondensates which contain 2,3-O-alkylidenetartaric acid derivatives, 2,3-O-alkylidene-L-threitol, furo[2,5] groups or terephthalates have the desired properties.

Surprisingly, the polycondensates showed a uniformly controllable active substance release with a strongly decreased "initial burst" when they were used for depot preparations of pharmaceuticals. In addition, nearly colorless soluble polycondensates could be prepared from the corresponding acid dichlorides.

The invention therefore relates to polycondensates which essentially contain at least 95 mol % of recurring structural units of the formula I

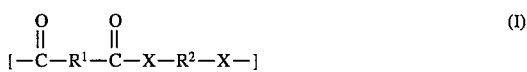

where R$^1$ is a) a compound of the formula II

where R$^5$ and R$^6$ are inert radicals, b) straight-chain or branched alkyl, alkenyl, cycloalkyl or cycloalkenyl which can be substituted by one or more inert radicals, c) aryl, mono- or polynuclear, mono- or polysubstituted by inert radicals, d) compounds of the formula V,

e) a heterocyclic radical which is mono- or poly nuclear and can be mono- or polysubstituted by inert radicals, where X is a) —O—, b) —NH— or c) —S—, where R$^2$ is a) a compound of the formula III

in which R$^5$ and R$^6$ have the abovementioned meaning, b) straight-chain or branched alkyl, alkenyl, cycloalkyl or cycloalkenyl which can be substituted by one or more inert radicals, c) mono- or polynuclear aryl, mono- or polysubstituted by inert radicals, d) a heterocyclic radical which is mono- or polynuclear and can be mono- or polysubstituted by inert radicals, or e) a compound of the formula VI

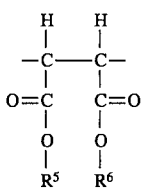

in which $R^5$ and $R^6$ have the abovementioned meaning, with the proviso that more than 5 mol % of the radicals $R^1$ and/or $R^2$ are present in the polycondensate of the formula I, where $R^1$ is a compound of the formula II and/or $R^2$ is a compound of the formula III, or in which more than 5 mol % of the radicals $R^1$ and $R^2$ are present in the polycondensate of the formula I, where a) $R^1$ is a compound of the formula V and $R^2$ is a compound of the formula VI, or b) $R^1$ is phenyl[1,2] phenyl[1,3] or phenyl[1,4] and $R^2$ is a compound of the formula VI.

The term "inert radical" is understood to mean substituents which do not react with one another under the preparation and processing conditions of the polycondensates according to the invention or are prevented from reacting with one another by protective groups. Inert radicals can be, for example, inorganic radicals, such as halogen, or they can also be organic radicals, such as alkyl, alkenyl, cycloalkyl, cycloalkenyl, alkoxy or dialkylaminoalkyl.

Functional groups which are prevented from reaction by protective groups are, for example, amino or hydroxyl.

Known protective groups are, for example, the benzyloxy or phenylsulfonyl groups.

Heterocyclic radicals can be mono- or polynuclear and in particular have one or two oxygen, nitrogen or sulfur atoms in the ring.

Aryl is an aromatic carbon ring. Polynuclear aryl radicals can be condensed with one another or linearly connected with one another via C-C bonds or via bridging groups, such as, for example, —O—, —COO—, —CH$_2$—, —CO—NH—, —S—, —CO— or an —SO$_2$— group.

Examples of polynuclear aromatic aryl radicals are 4,4'-biphenyl, naphthalene-1,5- or -2,6- groups or naphthalene-1,8- groups.

Preferred polycondensates of the formula I are those which essentially contain at least 95 mol % of recurring structural units of the formula I, where $R^1$ is a) straight-chain or branched ($C_1$–$C_{18}$)-alkyl or straight-chain or branched ($C_1$–$C_{18}$)-alkenyl which contains one or more double bonds, b) straight-chain or branched ($C_1$–$C_{18}$)-alkyl or straight-chain or branched ($C_1$–$C_{18}$)-alkenyl which contains one or more double bonds, mono- or polysubstituted by 1) ($C_5$–$C_7$)-cycloalkyl,
2) ($C_5$–$C_7$)-cycloalkenyl, having one or more double bonds,
3) halogen, such as fluorine or chlorine,
4) mercapto,
5) hydroxyl,
6) ($C_1$–$C_6$)-alkoxy,
7) phenoxy,
8) phenoxy, mono- or polysubstituted by
   8.1 halogen, such as fluorine, chlorine, bromine or iodine,
   8.2 ($C_1$–$C_6$)-alkyl,
   8.3 ($C_1$–$C_6$)-alkoxy,
   8.4 nitro or 8.5 carbethoxy,
9) naphthyloxy,
10) benzyloxy,
11) benzyloxy, mono- or polysubstituted in the aryl moiety by
   11.1 methoxy,
   11.2 carboxamido,
   11.3 amino,
   11.4 halogen, such as fluorine, chlorine, bromine or iodine,
   11.5 nitro or
   11.6 methyl,
12) amino,
13) monoalkylamino, having up to 7 carbon atoms,
14) monoalkylamino, having up to 7 carbon atoms, mono- or polysubstituted in the alkyl moiety by
   14.1 hydroxyl,
   14.2 carboxyl,
   14.3 carboxamide,
   14.4 carboethoxy,
   14.5 amino,
   14.6 ($C_1$–$C_6$)-alkylamino,
   14.7 di-($C_1$–$C_6$)-alkylamino,
   14.8 piperidine or
   14.9 morpholine,
15) dialkylamino having up to 7 carbon atoms, or
16) dialkylamino having up to 7 carbon atoms, substituted as defined in b) 14.1 to 14.9, c) aryl, having 6 to 14 carbon atoms, optionally mono- or disubstituted by
   1.1 ($C_1$–$C_6$)-alkyl,
   1.2 ($C_2$–$C_6$)-alkenyl,
   1.3 ($C_1$–$C_6$)alkylcarboxy,
   1.4 hydroxyl,
   1.5 halogen, such as fluorine, chlorine, bromine or iodine,
   1.6 acetoxy,
   1.7 ($C_1$–$C_6$)-alkylcarboxyamide,
   1.8 sulfonamide,
   1.9 nitro,
   1.10 ($C_1$–$C_6$)-alkoxy or
   1.11 amino, d) a compound of the formula IV

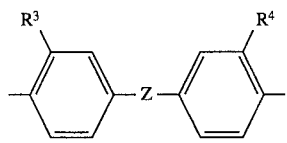

in which $R^3$ and $R^4$ independently of one another can be identical or different and are each
1) hydrogen or
2) an inert radical and Z is a compound from the group comprising
   1) —O—,
   2) —S—,
   3)

4) —SO$_2$—,

5)

6) —$C_nH_{2n}$—, in which n is an integer from 1 to 10 and the carbon chain can be straight or branched, or 7) —O—aryl—O, in which aryl is as defined in c), e) a compound of the formula II,

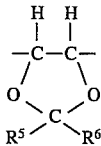

in which $R^5$ and $R^6$ independently of one another are
1) hydrogen,
2) alkyl or alkenyl having up to 18 carbon atoms,
3) alkyl or alkenyl having up to 18 carbon atoms, mono- or polysubstituted as defined in b) 1 to 16,
4) aryl, having 6 to 14 carbon atoms,
5) aryl, having 6 to 14 carbon atoms, mono- or polysubstituted as defined in c) 1.1 to 1.11, or f) a compound of the formula V

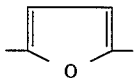

where X is
a) —O—,
b) —NH— or
c) —S—, where $R^2$ is
a) a compound of the formula III

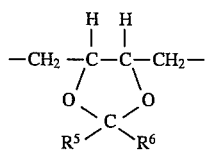

in which $R^5$ and $R^6$ have the abovementioned meanings, b) a compound of the formula VI,

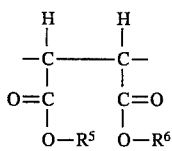

in which $R^5$ and $R^6$ have the abovementioned meanings, c) straight-chain- or branched alkyl or alkenyl having 1 to 18 carbon atoms, d) straight-chain or branched alkyl or alkenyl having 1 to 18 carbon atoms, mono- or polysubstituted by a radical from the group comprising
1) carboxyl,
2) carboxyl in which the hydroxyl group is replaced by a radical from the group comprising
  2.1 —O-($C_1$-$C_8$)-alkyl,
  2.2 halogen, such as fluorine or chlorine,
  2.3 —O-($C_1$-$C_4$)-alkylcarbonyl,
  2.4 ($C_1$-$C_6$)-alkylamino,
  2.5 ($C_1$-$C_6$)-alkylamino, mono- or polysubstituted in the alkyl moiety by a radical from the group comprising
    2.5.1 hydroxyl,
    2.5.2 mercapto or
    2.5.3. —O-($C_2$-$C_4$)-alkyl,
  2.6 genetically encodable L-amino acid,
  2.7 genetically encodable L-amino acid, mono- or polysubstituted by
    2.7.1 ($C_1$-$C_4$)-alkyl,
3) hydroxyl,
4) halogen, such as fluorine, chlorine, bromine or iodine,
5) amino,
6) mercapto or
7) alkyl having up to 8 carbon atoms, e) a cyclic compound of the formula VII

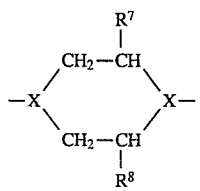

in which $R^7$ and $R^8$, independently of one another, are
1) hydrogen or
2) ($C_1$-$C_3$)-alkyl
and X is N, or f) aryl, having 5 to 14 carbon atoms, optionally mono- or disubstituted by
  1.1 ($C_1$-$C_6$)-alkyl,
  1.2 ($C_2$-$C_6$)-alkenyl,
  1.3 ($C_1$-$C_6$)-alkylcarboxy,
  1.4 hydroxyl,
  1.5 halogen, such as fluorine, chlorine, bromine or iodine,
  1.6 acetoxy,
  1.7 ($C_1$-$C_6$)-alkylcarboxamide,
  1.8 sulfonamide,
  1.9 nitro,
  1.10 ($C_1$-$C_6$)-alkoxy or
  1.11 amino, with the proviso that more than 5 mol % of the radicals $R^1$ and/or $R^2$ are present in the polycondensate of the formula I, where $R^1$ is a compound of the formula II and/or $R^2$ is a compound of the formula III, or in which more than 5 mol % of the radicals $R^1$ and $R^2$ are present in the polycondensate of the formula I, where a) $R^1$ is a compound of the formula V and $R^2$ is a compound of the formula VI, or b) $R^1$ is phenyl[1,2], phenyl[1,3] or phenyl[1,4] and $R^2$ is a compound of the formula VI.

Particularly preferred polycondensates of the formula I are those which essentially contain at least 95 mol % of recurring structural units of the formula I
where $R^1$ is a) a compound of the formula II, in which $R^5$ and $R^6$ independently of one another are
  1) hydrogen, with the proviso that $R^5$ and $R^6$ are not simultaneously hydrogen or,
  2) straight-chain or branched alkyl or alkylene having up to 18 carbon atoms, b) furo[2,5] or c) phenyl[1,4], phenyl[1,2], phenyl[1,3], X is a radical from the group comprising —O— and —NH—, where $R^2$ is
a) a compound of the formula III, in which $R^5$ and $R^6$ have the abovementioned meaning,
b) a compound of the formula VI, in which $R^5$ and $R^6$ have the abovementioned meaning,
c) a compound of the formula IX

where n is 3 or 4 and $R^6$ has the abovementioned meaning, with the proviso that more than 5 mol % of the radicals $R^1$ and/or $R^2$ are present in the polycondensate of the formula I, where $R^1$ is a compound of the formula II and/or $R^2$ is a compound of the formula III, or in which more than 5 mol % of the radicals $R^1$ and $R^2$ are present in the polycondensate of the formula I, where a) $R^1$ is a compound of the formula V and $R^2$ is a compound of the formula VI, or
b) $R^1$ is phenyl[1,2], phenyl[1,3] or phenyl[1,4] and $R^2$ is a compound of the formula VI.

To prepare the abovementioned polycondensates, a dicarboxylic acid dichloride of the formula X $$\text{ClOC}-R^1-\text{COCl} \quad (X)$$

is reacted with one or more of the diols, diamines, dithio compounds or diazines of the formula XI, XII, XIII or XIV

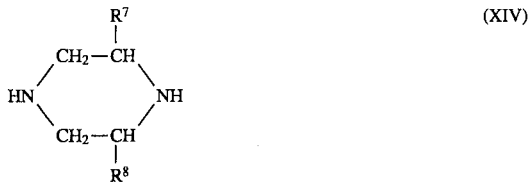

where $R^1$, $R^2$, $R^7$ and $R^8$ have the abovementioned meaning

The dicarboxylic acid dichloride of the formula X and the individual diol, diamine, dithio or diazine types of the formula XI, XII, XIII or XIV can also be employed in the form of mixtures with one another.

It is obvious to the person skilled in the art that the sum of all structural units derived from the dicarboxylic acids (A) and the sum of all structural units derived from the diols, dithio compounds, diamines and diazines (B) are essentially equal, i.e. that they differ by at most about 1%, preferably by at most 0.2%, and, in particular in the context of practical measurement and dosage possibilities, are equal.

The molecular weight of the resulting polyamides can be controlled, inter alia, by means of the selection of the proportions of A to B. These selection criteria are known to the person skilled in the art in the area of polycondensation.

Examples of suitable dicarboxylic acids, from which the dicarboxylic acid dichlorides of the formula X are derived, are 2,3-O-isopropylidene-L-tartaric acid, 2-chloroterephthalic acid, furandicarboxylic acid, 2-bromoterephthalic acid 2-methylterephthalic acid and in particular 2,3-O-isopropylidene-L-tartaric acid.

Examples of suitable diamines of the formula XII are lysine methyl ester, naphthalene-1,4-diamine, naphthalene-1,5-diamine, naphthalene-2,6-diamine and in particular lysine methyl ester or diazines.

Examples of suitable diols of the formula XI are diethyl tartrates, 2,3-O-isopropylidene-L-threitol or diisopropyl tartrate.

The condensation of the components described above is in general carried out in solution.

For this purpose, the monomeric compounds to be reacted with one another are as a rule dissolved in an organic solvent. The organic solvent in this case preferably contains at least one solvent, such as, for example, N-methyl-2-pyrrolidine, N,N-dimethylacetamide, pyridine, tetramethylurea, N-methyl-2-piperidone, dichloromethane, N,N'-dimethylethyleneurea, N-methylcaprolactam, N-acetylpyrrolidine, or N,N-dimethylpropyleneurea. For the process according to the invention, the preferred organic solvents pyridine, dichloromethane, furan or a mixture of these compounds is important.

In a preferred form of carrying out the solution polymerization, the monomers 2,3-O-isopropylidene-L-tartaric acid dichloride and diethyl tartrates are mixed with vigorous stirring in a mixture of pyridine and dichloromethane.

In the solution polymerization, the polycondensation temperatures are customarily between $-20°$ C. and $+120°$ C., preferably between $+10°$ C. and $+100°$ C. Particularly good results are obtained at reaction temperatures between $+10°$ C. and $+80°$ C.

The sum of the concentrations of the monomeric compounds in the polymerization mixture solution can be adjusted taking into consideration the desired degree of polymerization, the desired viscosity of the polymerization mixture, the nature of the monomeric compounds used, the nature of the solvent used, and the desired polymerization temperature. The most favorable sum of the concentrations can in this case be determined on the basis of a number of preliminary experiments for the course of the polymerization.

Polycondensation reactions are preferably carried out such that, after conclusion of the reaction, 2 to 15, preferably 5 to 15% by weight, of polycondensate is present in the solution. Particularly good results are obtained at concentrations of 5.0 to 10% by weight.

In the course of the polycondensation, the molecular weight of the polymer grows and with it also the viscosity of the reaction mixture. Molecular weights of 500 to 1,000,000 are reached, preferably 3,000 to 100,000. As a rule, viscosities of more than 0.1 dl.g$^{-1}$ (Staudinger index, dimethylformamide, 25° C.) are reached.

If the polymer solution has reached the viscosity necessary for further processing, the polycondensation can be stopped in a customary manner by addition of monofunctional compounds, such as, for example, acetyl chloride. The hydrogen chloride formed and loosely bound to the amide solvent can then be neutralized by addition of basic substances. Those suitable for this purpose are, for example, pyridine, triethylamine, and morpholine, but in particular pyridine.

The 2,3-O-alkylidene-L-tartaric acid dichlorides which can be employed as the starting substance are obtained, for example, by reaction of alkyl tartrates with 2,2-dimethoxypropane to give the corresponding dialkyl tartrate acetone ketals analogously to the reactions described by M. Carmack et al. (J. Org. Chem. 33, 1968, pages 2171–2173). These dialkyl tartrate acetone ketals are converted into the corresponding salts using alkali metal hydroxides and finally converted into the corresponding L-tartaric acid dichloride derivatives by reaction with phosphorus trichloride, phosphorus pentachloride, oxalyl chloride or thionyl chloride.

2,3-O-Alkylidene-L-threitol is prepared, for example, by reaction of dialkyl tartrate acetone ketal with LiAlH$_4$ to give the corresponding 2,3-O-alkylidene-2-threitol (P. W. Felt, J. Med. Chem. 7, 1964, pages 14–17).

Furandicarboxylic acid dichlorides are obtainable, for example, by the process described by Moore and Kelley (American Chemical Society, 1'1, No. 3, 1978, pages 568–573).

The invention further relates to ultrasonic contrast agents composed of microparticles which contain a gas and a polycondensate of the formula I.

Art advantageous process for the preparation of ultrasonic contrast agent from the polycondensates according to the invention consists in dissolving one or more of the polycondensates of the formula I in a solvent or solvent mixture having a high melting point or mixing these derivatives with one or more further polymers and/or physiologically acceptable auxiliaries and dissolving the mixture in a solvent or solvent mixture having a high melting point and adding the solution dropwise to a condensed cold gas, for example, liquid nitrogen. Owing to the Leidenfrost phenomenon, round particles are formed. Solvents which can be employed are, for example, dimethylformamide, dimethyl sulfoxide, dioxane or mixtures with alcohols. The high-melting and water-miscible solvent is dissolved out, for example, by transferring the microparticles into water and precipitating the polymer in this way, the spherical shape of the microparticles being retained.

If, in addition to a high melting point, the organic solvent used at the same time has a low boiling point, this process of dropwise addition can be further simplified in that the solvent, for example dioxane, can be carefully removed directly by means of freeze drying.

Another process for the preparation of ultrasonic contrast agent from the polymer according to the invention consists in dissolving one or more of the polycondensates of the formula I in a solvent or solvent mixture and precipitating them, if appropriate after addition of a further solvent and/or of one or more further polymers, or dispersing them in water. Suitable further polymers are, for example, polyvinyl alcohol (®Mowiol 28–99) or polyoxyethylenepolyoxypropylene (®Pluronic F 127). The further solvent used can be, for example, ether. Microparticles having a diameter of 0.5 to 15 µm are obtained by vigorous stirring, for example with a mixer (25,000 rpm). The solvents are then removed, for example by lyophilizing.

A particularly advantageous process consists in obtaining the micro-particles by spray drying. For this purpose, one or more compounds of the formula I are dissolved or these compounds are mixed with one or more other polymers and/or physiologically acceptable auxiliaries and brought into solution. Suitable solvents or solvent mixtures are, for example, tetrahydrofuran, methylene chloride, furan, DMSO (dimethyl sulfoxide), dioxane or acetone. The solution is then sprayed into a spray dryer to give microparticles.

In the process described, the polymers of the formula I can be used on their own or alternatively as a mixture of various polymers of the formula I. These polymers can also be employed in mixtures with other biodegradable and/or biocompatible polymers (for example ®Pluronic F68, PHEA, dextrans, polyethylene glycols, hydroxyethylstarch and other degradable or precipitatable polysaccharides) or physiologically acceptable auxiliaries (for example polymer plasticizers or DMSO).

The micro-particles contain gases, for example air, nitrogen, rare gases such as helium, neon, argon or krypton, hydrogen, carbon dioxide, oxygen or mixtures thereof. The micro-particles are loaded with a gas, for example by storing the micro-particles after lyophilization in an appropriate gas atmosphere or, in the case of spray drying, obtaining them directly, during preparation, in an appropriate gas atmosphere.

The invention further relates to a diagnostic or therapeutic agent containing at least one ultrasonic contrast agent according to the invention in addition to physiologically acceptable and pharmacologically suitable excipients and, if appropriate, other additives and/or auxiliaries.

Before administration, the ultrasonic contrast agents are converted into a suitable diagnostic or therapeutic administration form by addition of one or more physiologically acceptable excipients and, if appropriate, other additives and/or auxiliaries. The ultrasonic contrast agents are suspended, for example by addition of water and mixing, before administration.

By addition of osmotically active substances, for example sodium chloride, galactose, glucose, fructose, it is possible to produce physiological isotonicity of the particle suspension.

In the described processes for the preparation of the ultrasonic contrast agents, particle sizes can be achieved in which 90% of the particles are between 0.1 µm and 10 µm. Using the spray drying process, particle size distributions can be achieved in which 90% of the particles are smaller than 3 µm. Larger particles are removed by sieving, for example using a 15 µm sieve netting and/or 3 µm sieve netting. When using these micro-particles as ultrasonic contrast agents for the diagnosis of cardiovascular diseases, particle sizes from 0.1 µm to 7 µm have proved suitable, advantageously particle sizes from 0.1 µm to 3 µm are employed. The ultrasonic contrast agents are injected, for example, into the bloodstream. Per injection, 0.1 mg to 1,000 mg of the micro-particles, preferably 1 mg to 100 mg, are employed.

The ultrasonic contrast agents described in the foregoing can be used both for diagnostic and therapeutic methods. The use of the ultrasonic contrast agents according to the invention is not restricted only to the visualization of the bloodstream in the right ventricular part of the blood circulation after venous administration. The ultrasonic contrast agents can be used with excellent effect for the investigation of the left side of the heart. In addition, it is also possible with these contrast agents to visualize other organs supplied by the blood, such as the liver, spleen, kidneys, brain or myocardium.

The ultrasonic contrast agents are also suitable, however, for the visualization of cavities in humans, animals or plants, for example the urinary bladder, ureter, uterus or vagina.

Some of the polyamides according to the invention are thermoplastic and are therefore suitable for the production of active substance depot forms by various methods, such as, for example, by compression, extrusion, precipitation, spraying, etc.

Implantable particles, in particular microcapsules and microspheres and also, by compaction, macroscopic shaped articles of any geometry, in particular tablets and rods, can be prepared by known methods from the polycondensates according to the invention. Degradation experiments in vitro with the polycondensates of the formula I according to the invention have shown that the degradation proceeds via functional side groups, ring opening and parent chain degradation.

The following examples describe the invention in detail. Percentages relate to the weight, if not stated otherwise.

EXAMPLE 1

Dimethyl 2,3-O-isopropylidene-L-tartrate

A mixture of 101 g (0.673 mol) of L-tartaric acid, 160 g (1.54 mol) of 2,2-dimethoxypropane (Aldrich), 40 ml of anhydrous methanol and 0.4 g of p-toluenesulfonic acid monohydrate is cautiously heated under reflux and stirred for 1.5 hours. The dark red homogenous solution is additionally mixed with 79.5 g (0.764 mol) of 2,2-dimethoxypropane and 450 ml of cyclohexane. The resulting two-phase mixture is heated under reflux and the acetone/cyclohexane and the methanol/cyclohexane azeotropes are carefully removed. After 47 hours, 590 ml of distillate are obtained. This is neutralized with anhydrous potassium carbonate (1 g). The solvent is distilled off and 148.3 g of dimethyl 2,3-O-isopropylidene-L-tartrate are obtained as a pale yellow liquid. Boiling point 82°–90° C.; $[\alpha]_D^{20}$ –49°.

EXAMPLE 2

2,3-O-Isopropylidene-L-threitol

A suspension of $LiAlH_4$ (42 g) in diethyl ether (400 ml) is boiled under reflux while stirring vigorously. A solution of dimethyl 2,3-O-isopropylidene-L-tartrate (123 g) from Example 1 in diethyl ether (500 ml) is added dropwise to the $LiAlH_4$ suspension without heating over the course of 2 hours. After heating for a further 3 hours, ethyl acetate (30 ml) is added and the reaction solution is cooled to 0°–5° C. After the addition of water (42 ml), 4 NNaOH (42 ml) and water (130 ml), the precipitated residue is removed by filtration and extracted with ether. The ether extracts are combined and dried over anhydrous $MgSO_4$, and the ether is then evaporated. Distillation of the residue gives 64 g of 2,3-O-isopropylidene-L-threitol;

Boiling point 96°–96.5° C.; $[\alpha]_D^{20}$ +4.1°.

EXAMPLE 3

2,3-O-Isopropylidene-L-dipotassium tartrate 20 g of dimethyl tartrate acetone ketal (91 mmol), 15 g of KOH p.a. (270 mmol), 60 ml of distilled water and 120 ml of ethanol (p.a.) are heated under reflux. After about 4 hours, the reaction solution is concentrated, the residue is dissolved in a little water and the solution is precipitated in ice-cooled ethanol. After a second precipitation the batch is dried to constant weight.

White crystalline substance; yield: 23 g corresponding to 95% of theory.

$^1$H-NMR (100 MHz) in $D_2O$: Singlet 1.43 ppm, 6H, —C$\underline{H}_3$ Singlet 4.46 ppm, 2H, —CH

EXAMPLE 4

2,3-O-Isopropylidene-L-tartaric acid dichloride 15 g of 2,3-O-isopropylidene-L-dipotassium tartrate (56 mmol) are cautiously reacted (strong evolution of heat) with 30 ml of thionyl chloride which has previously been distilled over cottonseed oil. On stirring overnight the batch solidifies, from which solid the excess thionyl chloride is then distilled off. The distillation of the acid chloride is then carried out in an oil pump vacuum (b.p.$_{0.01bar}$: 75°–80° C.).

Colorless liquid; yield: 8.3 g corresponding to 65% of theory.

| Elemental analysis: | % C | % H | % Cl | % S |
|---|---|---|---|---|
| calc. | 37.0 | 3.5 | 31.3 | 0 |
| found | 37.2 | 3.6 | 31.4 | <0.3 |

$^1$H-NMR (100 MHz) in $CDCl_3$: Singlet 1.50 ppm, 6H, —C$\underline{H}_3$ Singlet 5.18 ppm, 2H, —CH

EXAMPLE 5

2',3'-(1',4'-Diethyl)-L-tartryl poly-(2,3-O-isopropylidene)-L-tartrate a) 2.88 g of 2,3-O-isopropylidene-L-tartaric acid dichloride (12.7 mmol), 2,61 g of diethyl tartrate (12.7 mmol), 2.1 ml of pyridine and 50 ml of dried dichloromethane are mixed and stirred for 3 days. A white precipitate is formed during the course of this. To complete the reaction, the mixture is stirred for a further day under reflux and then precipitated in dry diisopropyl ether at –20° C. After filtering off with suction and drying, the precipitate is dissolved in tetrahydrofuran (THF) and precipitated in water, filtered off with suction again and dried in vacuo.

White powder; yield: 3.4 g corresponding to 78% of theory.

| Elemental analysis: | % C | % H |
|---|---|---|
| calc. | 50.0 | 5.5 |
| found | 49.4 | 5.5 |

$^1$H-NMR (300 MHz) in $CDCl_3$: Triplet 1.26 ppm, 6H, —CH$_2$C$\underline{H}_3$ Singlet 1.45 ppm, 6H, —CH$_3$ Quadruplet 4,20 ppm, 4H, —CH$_2$—CH$_3$ Singlet 5.05 ppm, 2H Singlet 5.82 ppm, 2H Molecular weight 15,000 ($M_w$) (after prior calibration under gel permeation chromatography (GPC) by means of oligomers):

b) 2.59 g 2,3-O-isopropylidene-L-tartaric acid dichloride (11.4 mmol) and 2.87 g of diethyl tartrate (13.9 mmol) are reacted with one another as in a). The final product has a molecular weight of 3,500 (determined by means of GPC).

c) Viscosity measurements The viscosity measurement is carried out using a micro-Ubbelohde capillary viscometer from Schott. To determine the Staudinger index, the relative viscosities are measured in dimethylformamide at 25° C. in a concentration-dependent manner between 0.01 and 0.1 g/dl as in Schacht et al. Taking into account an effect discussed as "wall adsorption" (B. Vollmert, Grundriβ der Makromolekularen Chemie (Outline of Macromolecular Chemistry), E. Vollmert publishers Karlsruhe Vol. III, p. 70, 1982), a Staudinger index of (n)=0.9 dl/g and, with an oligomer of $M_{gpc}$=3,500 (see Example 5b), (n)=0.5 dl/g results as the viscosity of 2',3'-(1',4'-diethyl)-L-tartryl poly-(2,3-O-isopropylidene)-L-tartrate prepared as in Example 5a) and having a molecular weight determined by gel permeation chromatography of 15,000. The last-mentioned oligomer had a degree of polymerization of about 10. This excludes the fact that, under the conditions described, an oligomer having a viscosity of 0.04 dl/g exists.

EXAMPLE 6

2',3'-O-Isopropylidene-L-threityl poly-(2,3-O-isopropylidene)-L-tartrate 5.20 g of 2,3-O-isopropylidene-L-tartaric acid dichloride (22.9 mmol), 3.71 g of 2,3-O-isopropylidene-L-threitol (22.9 mmol), 3.7 ml of pyridine and 100 ml of dried dichloromethane are mixed and worked up analogously to Example 5.

Slightly colored product; yield: 5.7 g corresponding to 80% of theory.

Molecular weight 65,000 ($M_w$) (after prior calibration under GPC by means of oligomers):

$^1$H-NMR (300 MHz) in $CDCl_3$: Singlet 1.41 ppm, 6H, —$CH_3$ Singlet 1.48 ppm, 6H, —$CH_3$ Singlet 4.10 ppm, 2H, —CH Multiplet 4.35 ppm, 4H, —$CH_2$ Singlet 4.87 ppm, 2H, —CH

EXAMPLE 7

2',3'-(1',4'-Diisopropyl)-L-tartryl poly-(2,3-O-isopropylidene)-L-tartrate 10.48 g of 2,3-O-isopropylidene-L-tartaric acid dichloride (46.3 mmol), 10.8 g of diisopropyl L-tartrate (46.2 mmol), 7.5 ml of pyridine and 200 ml of dried dichloromethane are mixed and additionally worked up analogously to Example 5.

Yield: 11.3 g corresponding to 63% of theory.

EXAMPLE 8

2,3-(1,4-Diethyl)-L-tartryl polyfurandicarboxylate 12.01 g of furandicarboxylic acid dichloride (62.2 mmol), 12.82 g of diethyl tartrate (62.2 mmol), 10 ml of dried pyridine and 200 ml of dried dichloromethane are mixed and additionally worked up analogously to Example 5.

White powder; yield: 15 g corresponding to 74% of theory.

$^1$H-NMR (300 MHz) in $CDCl_3$: Triplet 1.22 ppm, 6H, —$CH_3$ Quadruplet 4.27 ppm, 4H, $CH_2$—$CH_3$ Singlet 6.00 ppm, 2H, —CH Singlet 7.35 ppm, 2H, =$CH_{arom.}$

EXAMPLE 9

Poly-(2,3-(1,4-diethyl)-L-tartryl) terephthalate 8.81 g of terephthaloyl chloride (43.4 mmol), 8.95 g of diethyl tartrate (43.4 mmol), 7 ml of pyridine and 180 ml of dried dichloromethane are mixed and additionally processed analogously to Example 6.

Yield: 13.6 g corresponding to 94% of theory.

$^1$H-NMR (300 MHz) in $CDCl_3$: Triplet 1.19 ppm, 6H, —$CH_3$ Quadruplet 4.22 ppm, 4H, —$CH_2$—$CH_3$ Singlet 6.03 ppm, 2H, —CH Singlet 8.20 ppm, 4H, =$CH_{arom.}$

EXAMPLE 10

Polylysine methyl ester 2,3-O-isopropylidene-L-tartramide 5.3 g of $Na_2CO_3$ are dissolved in 70 ml of water, 3.0 g of lysine methyl ester are dissolved in 20 ml of water and 1 ml of 2,3-O-isopropylidene-L-tartaric acid dichloride is dissolved in 90 ml of dichloromethane. The two aqueous solutions are mixed together and vigorously stirred and the organic phase is added immediately afterwards. A precipitate slowly forms. After 10 minutes, the dichloromethane is removed in a rotary evaporator and the precipitate is washed several times with water.

Yield: 1.1 g.

$^1$H-NMR (100 MHz) in DMSO-$d_6$: broad signal around 1.35 ppm, 10H, —$CH_3$, —$NHCH_2$—$CH_2$—$CH_2$ broad signal around 1.70 ppm, 2H, —$CH_2$—CH broad signal around 3.08 ppm, 2H, —NH—$CH_2$ Singlet 3.61 ppm, 3H, —$OCH_3$ Multiplet 4–4.7 ppm, 3H, —CH broad signals 7.6–8.5 ppm, 2H, —CONH

EXAMPLE 11

Preparation of active substance-containing micro-particles 4 g of 2',3'-(1',4'-diethyl)-L-tartryl poly-(2,3-O-isopropylidene)-L-tartrate (Example 5) are dissolved to 10% in the solvents indicated in Table 1 and the solution is mixed with 0.2 g of the peptide active substance buserelin, dissolved in 1 ml of water. The suspensions/solutions are then sprayed to give micro-particles in a spray dryer (Mini Spray Dryer Büchi 190, W.Germany).

Typical spray parameters are given in Table 2.

TABLE 1

| Solvent | Particle size | Active substance loading | Initial active substance release |
|---|---|---|---|
| THF | 8 μm | 4% | 55% |
| $CH_2Cl_2$ | 4 μm | 3.6% | 25% |
| Furan | 5 μm | 3.4% | 20% |
| Acetone | 3 μm | 4.2% | 10% |

TABLE 2

| Inlet temperature | 61° C. | Nozzle air pressure | 2.8 bar |
|---|---|---|---|
| Outlet temperature | 45° C. | Nozzle air flow | 300 Nl/h |
| Heating | 2.2 scale divisions | Pressure in the filter | −25 mbar |
| Pump setting | 10 | Aspirator setting | 10 |

An amount of polymer (85–100 mg) in each case equivalent to 3.6 μg of buserelin is dispersed in a suspending auxiliary consisting of 150 mg of Dextran 40 (Roth, W. Germany), 7.5 mg of polysorbate and 13.5 mg of NaCl in 1.5 ml of distilled water. The suspension is completely pressed through a 15 μm sieve netting and then lyophilized. Before administration, the micro-particles are resuspended using water.

The size of the micro-particles has been determined in a Cilas Granulometer 715, the active substance loading by means of HPLC and the initial active substance release with the aid of an in vitro test. For the in vitro test, 20 mg of micro-particles were dispersed in 5 ml of suspending auxiliary (s.o.) and kept in suspension by stirring vigorously in rolled flange bottles with magnet stirrers for 24 hours. The solid is then filtered off and the amount of active substance which has escaped from the micro-particles is determined in the filtrate.

EXAMPLE 12

Production of rod-shaped implants (rods)

An intimate mixture of pulverulent polycondensates according to the invention, additives and active substance(s) is heated above the softening point in a suitable device, for example an extruder for thermoplastics, a moldable material being formed. Additives and active substance(s) are homogeneously dispersed in the softened polymer by kneading and the polymer/active substance suspension obtained is pressed through a nozzle of suitable diameter (>0.5 mm). On cooling, the strip of the extruded polymer/active substance suspension solidifies to give a solid, rod-shaped aggregate whose active substance content is determined from its length and its diameter.

We claim:

1. A method for investigating or treating an animal or plant organism comprising administering to said organism microparticles of a compound comprising:

a polycondensate compound which contains at least 95 mol % of recurring structural units of the formula I

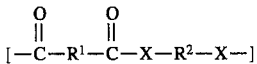     (I)

where $R^1$ is a) straight-chain or branched $(C_1-C_{18})$-alkyl or straight-chain or branched $(C_1-C_{18})$-alkenyl which contains one or more double bonds, b) straight-chain or branched $(C_1-C_{18})$-alkyl or straight-chain or branched $(C_1-C_{18})$-alkenyl which contains one or more double bonds, mono- or polysubstituted by
 1) $(C_5-C_7)$-cycloalkyl,
 2) $(C_5-C_7)$-cycloalkenyl, having one or more double bonds,
 3) halogen,
 4) mercapto,
 5) hydroxy,
 6) $(C_1-C_6)$-alkoxy,
 7) phenoxy,
 8) phenoxy, mono- or polysubstituted by
  8.1 halogen,
  8.2 $(C_1-C_6)$-alkyl,
  8.3 $(C_1-C_6)$-alkoxy,
  8.4 nitro or
  8.5 carbethoxy,
 9) naphthyloxy,
 10) benzyloxy,
 11) benzyloxy, mono- or polysubstituted in the aryl moiety by
  11.1 methoxy,
  11.2 carboxamid,
  11.3 amino,
  11.4 halogen,
  11.5 nitro or
  11.6 methyl,
 12) amino,
 13) monoalkylamino, having 1 to 7 carbon atoms,
 14) monoalkylamino, having 1 to 7 carbon atoms, mono- or polysubstituted in the alkyl moiety by
  14.1 hydroxyl,
  14.2 carboxyl,
  14.3 carboxamide,
  14.4 carboethoxy,
  14.5 amino,
  14.6 $(C_1-C_6)$-alkylamino,
  14.7 di-$(C_1-C_6)$-alkylamino,
  14.8 piperidine or
  14.9 morpholine,
 15) dialkylamino having 1 to 7 carbon atoms, or
 16) dialkylamino having 1 to 7 carbon atoms, substituted as defined in b) 14.1 to 14.9, c) aryl, having 6 to 14 carbon atoms, optionally mono- or disubstituted by
 1.1 $(C_1-C_6)$-alkyl,
 1.2 $(C_2-C_6)$-alkenyl,
 1.3 $(C_1-C_6)$alkylcarboxy,
 1.4 hydroxyl,
 1.5 halogen,
 1.6 acetoxy,
 1.7 $(C_1-C_6)$-alkylcarboxamide,
 1.8 sulfonamide,
 1.9 nitro,
 1.10 $(C_1-C_6)$-alkoxy or
 1.11 amino, d) a compound of the formula IV

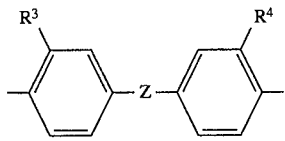     (IV)

in which $R^3$ and $R^4$ independently of one another are
1) hydrogen or
2) an inert radical and
wherein Z is a compound
 1) —O—,
 2) —S—,
 3)

4) —SO$_2$—
 5)

6) —$C_nH_{2n}$—, in which n is an integer from 1 to 10 and the carbon chain is straight or branched, or
 7) —O-aryl-O, in which aryl is as defined in c), e) a compound of the formula II,

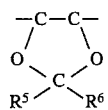     (II)

in which $R^5$ and $R^6$ independently of one another are
1) hydrogen,
2) alkyl or alkenyl having 1 to 18 carbon atoms,
3) alkyl or alkenyl having 1 to 18 carbon atoms, mono- or polysubstituted as defined in b) 1 to 16,
4) aryl, having 6 to 14 carbon atoms,
5) aryl, having 6 to 14 carbon atoms, mono- or polysubstituted as defined in c) 1.1 to 1.11, or f) a compound of the formula V

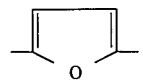     (V)

where X in formula I is
a) —O—,
b) —NH— or
c) —S—,
where $R^2$ in formula I is a) a compound of the formula III

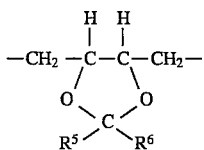 (III)

in which $R^5$ and $R^6$ have the above-mentioned meanings, b) a compound of the formula VI,

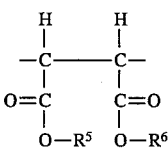 (VI)

in which $R^5$ and $R^6$ have the above-mentioned meanings, c) straight-chain or branched alkyl or alkenyl having 1 to 18 carbon atoms, d) straight-chain or branched alkyl or alkenyl having 1 to 18 carbon atoms, mono- or polysubstituted by a radical wherein said radical is
1) carboxyl,
2) carboxyl in which the hydroxyl group is replaced by a radical wherein said radical is
   2.1 —O-($C_1$–$C_8$)-alkyl,
   2.2 halogen,
   2.3 —O-($C_1$–$C_4$)-alkylcarbonyl,
   2.4 ($C_1$–$C_6$)-alkylamino,
   2.5 ($C_1$–$C_6$)-alkylamino, mono- or polysubstituted in the alkyl moiety by a radical wherein said radical is
      2.5.1 hydroxyl,
      2.5.2 mercapto,
      2.5.3. —O-($C_2$–$C_4$)-alkyl,
   2.6 L-amino acid or genetically encoded L-amino acid,
   2.7 L-amino acid or genetically encoded L-amino acid, either of which is mono- or polysubstituted by
      2.7.1 ($C_1$–$C_4$)-alkyl
3) hydroxyl,
4) halogen,
5) amino,
6) mercapto or
7) alkyl having 1 to 8 carbon atoms, e) a cyclic compound of the formula VII

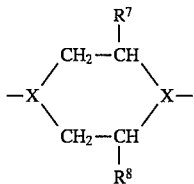 (VII)

in which $R^7$ and $R^8$, independently of one another, are
1) hydrogen or
2) ($C_1$–$C_3$)-alkyl
and X is N, or f) aryl, having 5 to 14 carbon atoms, optionally mono- or disubstituted by
1.1 ($C_1$–$C_6$)-alkyl,
1.2 ($C_2$–$C_6$)-alkenyl,
1.3 ($C_1$–$C_6$)-alkylcarboxy,
1.4 hydroxyl,
1.5 halogen,
1.6 acetoxy,
1.7 ($C_1$–$C_6$)-alkylcarboxamide,
1.8 sulfonamide,
1.9 nitro,
1.10 ($C_1$–$C_6$)-alkoxy or
1.11 amino, with the proviso that more than 5 mol % of the radicals $R^1$ and/or $R^2$ are present in the polycondensate of the formula I, where $R^1$ is a compound of the formula II or is a compound $R^2$ of the formula III, or $R^1$ is a compound of the formula II and $R^2$ is a compound of the formula III, or in which more than 5 mol % of the radicals $R^1$ and $R^2$ are present in the polycondensate of the formula I, where a) $R^1$ is a compound of the formula V and $R^2$ is a compound of the formula VI, or;

b) $R^1$ is phenyl 1,2; phenyl 1,3 or phenyl 1,4 and $R^2$ is a compound of the formula VI, and with the further proviso that when R1 is a compound of the formula II and both R5 and R6 in formula II are hydrogen, X together with R2 in formula I is not —NH— together with C6-alkyl or —NH— together with xylylene;
wherein said microparticles contain a gas or a therapeutic agent.

2. The method of claim 1 wherein said polycondensate is 2',3'-(1',4'-diethyl)-L-tartryl poly-(2,3-O-isopropylidene)-L-tartrate.

3. The method of claim 1 wherein said polycondensate is 2',3'-O-isopropylidene-L-threityl poly-(2,3-O-isopropylidene-L-tartrate.

4. The method of claim 1 wherein said polycondensate is 2',3'-(1',4'-diisopropyl)-L-tartryl poly-(2,3,-O-isopropylidene)-L-tartrate.

5. The method of claim 1 wherein said polycondensate is 2,3-(1,4-diethyl)-L-tartryl polyfurandicarboxylate.

6. The method of claim 1 wherein said polycondensate is poly-(2,3-(1,4-diethyl)-L-tartryl) terephthalate.

7. The method of claim 1 wherein said polycondensate is polylysine methylester 2,3,-O-isopropylidene-L-tartramide.

8. A method for investigating an animal or plant organism according to any one of claims 1–7 wherein said microparticles contain a gas, administering said microparticles containing a gas to said organism, and exposing said organism to ultrasound to produce a visual image of said organism.

9. A method of any one of claims 1 to 7 for treating an animal or plant organism wherein said microparticles contain a therapeutic agent.

10. A method of treating an animal organism according to any one of claims 1 to 7 where said organism comprises a mamalian organism comprising administering to said organism microparticles containing a therapeutic agent comprising buserelin.

11. A controlled release composition of matter comprising a therapeutic agent and a compound comprising:
a polycondensate compound which contains at least 95 mol % of recurring structural units of the formula I

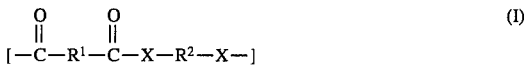 (I)

where $R^1$ is
a) straight-chain or branched ($C_1$–$C_{18}$)-alkyl or straight-chain or branched ($C_1$–$C_{18}$)-alkenyl which contains one or more double bonds, b) straight-chain or branched ($C_1$–$C_{18}$)-alkyl or straight-chain or branched ($C_1$–$C_{18}$)-alkenyl which contains one or more double bonds, mono- or polysubstituted by 1) $(C_5-C_7)$-cycloalkyl,
2) $(C_5-C_7)$-cycloalkenyl, having one or more double bonds,
3) halogen,
4) mercapto,
5) hydroxy,
6) $(C_1-C_6)$-alkoxy,
7) phenoxy,
8) phenoxy, mono- or polysubstituted by
   8.1 halogen,
   8.2 $(C_1-C_6)$-alkyl,
   8.3 $(C_1-C_6)$-alkoxy,
   8.4 nitro or
   8.5 carbethoxy,
9) naphthyloxy,
10) benzyloxy,
11) benzyloxy, mono- or polysubstituted in the aryl moiety by
   11.1 methoxy,
   11.2 carboxamid,
   11.3 amino,
   11.4 halogen,
   11.5 nitro or
   11.6 methyl,
12) amino,
13) monoalkylamino, having 1 to 7 carbon atoms,
14) monoalkylamino, having 1 to 7 carbon atoms, mono- or polysubstituted in the alkyl moiety by
   14.1 hydroxyl,
   14.2 carboxyl,
   14.3 carboxamide,
   14.4 carboethoxy,
   14.5 amino,
   14.6 $(C_1-C_6)$-alkylamino,
   14.7 di-$(C_1-C_6)$-alkylamino,
   14.8 piperidine or
   14.9 morpholine,
15) dialkylamino having 1 to 7 carbon atoms, or
16) dialkylamino having 1 to 7 carbon atoms, substituted as defined in b) 14.1 to 14.9, c) aryl, having 6 to 14 carbon atoms, optionally mono- or disubstituted by
   1.1 $(C_1-C_6)$-alkyl,
   1.2 $(C_2-C_6)$-alkenyl,
   1.3 $(C_1-C_6)$alkylcarboxy,
   1.4 hydroxyl,
   1.5 halogen,
   1.6 acetoxy,
   1.7 $(C_1-C_6)$-alkylcarboxamide,
   1.8 sulfonamide,
   1.9 nitro,
   1.10 $(C_1-C_6)$-alkoxy or
   1.11 amino, d) a compound of the formula IV

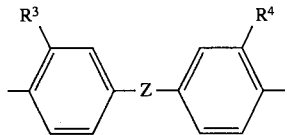

in which $R^3$ and $R^4$ independently of one another are
1) hydrogen or
2) an inert radical and
wherein Z is a compound
1) —O—,
2) —S—,

3)

$$-\overset{O}{\underset{\|}{C}}-,$$

4) —SO$_2$—

5)

$$-\overset{O}{\underset{\|}{C}}-O-,$$

6) —$C_nH_{2n}$—, in which n is an integer from 1 to 10 and the carbon chain is straight or branched, or
7) —O-aryl-O, in which aryl is as defined in c), e) a compound of the formula II, $$\begin{array}{c} -C-C- \\ O \diagdown \diagup O \\ C \\ R^5 \diagup \diagdown R^6 \end{array} \quad (II)$$

in which $R^5$ and $R^6$ independently of one another are
1) hydrogen,
2) alkyl or alkenyl having 1 to 18 carbon atoms,
3) alkyl or alkenyl having 1 to 18 carbon atoms, mono- or polysubstituted as defined in b) 1 to 16,
4) aryl, having 6 to 14 carbon atoms,
5) aryl, having 6 to 14 carbon atoms, mono- or polysubstituted as defined in c) 1.1 to 1.11, or f) a compound of the formula V $$\begin{array}{c} \text{(V)} \\ \diagup\diagdown \\ O \end{array}$$

where X in formula I is
a) —O—,
b) —NH— or
c) —S—,
where $R^2$ in formula I is
a) a compound of the formula III $$-CH_2-\overset{H}{\underset{|}{C}}-\overset{H}{\underset{|}{C}}-CH_2- \quad (III)$$
$$\begin{array}{c} O \diagdown \diagup O \\ C \\ R^5 \diagup \diagdown R^6 \end{array}$$

in which $R^5$ and $R^6$ have the above-mentioned meanings, b) a compound of the formula VI, $$\begin{array}{c} H & H \\ | & | \\ -C------C- \\ | & | \\ O=C & C=O \\ | & | \\ O-R^5 & O-R^6 \end{array} \quad (VI)$$

in which $R^5$ and $R^6$ have the above-mentioned meanings, c) straight-chain or branched alkyl or alkenyl having 1 to 18 carbon atoms, d) straight-chain or branched alkyl or alkenyl having 1 to 18 carbon atoms, mono- or polysubstituted by a radical wherein said radical is
1) carboxyl,
2) carboxyl in which the hydroxyl group is replaced by a radical wherein said radical is 2.1 —O-($C_1$–$C_8$)-alkyl,
2.2 halogen,
2.3 —O-($C_1$–$C_4$)-alkylcarbonyl,
2.4 ($C_1$–$C_6$)-alkylamino,
2.5 ($C_1$–$C_6$)-alkylamino, mono- or polysubstituted in the alkyl moiety by a radical wherein said radical is
  2.5.1 hydroxyl,
  2.5.2 mercapto,
  2.5.3 —O-($C_2$–$C_4$)-alkyl,
2.6 L-amino acid or genetically encoded L-amino acid,
2.7 L-amino acid or genetically encoded L-amino acid, either of which is mono- or polysubstituted by
  2.7.1 ($C_1$–$C_4$)-alkyl
3) hydroxyl,
4) halogen,
5) amino,
6) mercapto or
7) alkyl having 1 to 8 carbon atoms,
e) a cyclic compound of the formula VII

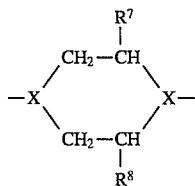
(VII)

in which $R^7$ and $R^8$, independently of one another are
1) hydrogen or
2) ($C_1$–$C_3$)-alkyl
and X is N, or
f) aryl, having 5 to 14 carbon atoms, optionally mono- or disubstituted by
  1.1 ($C_1$–$C_6$)-alkyl,
  1.2 ($C_2$–$C_6$)-alkenyl,
  1.3 ($C_1$–$C_6$)-alkylcarboxy,
  1.4 hydroxyl,
  1.5 halogen,
  1.6 acetoxy,
  1.7 ($C_1$–$C_6$)-alkylcarboxamide,
  1.8 sulfonamide,
  1.9 nitro,
  1.10 ($C_1$–$C_6$)-alkoxy or
  1.11 amino,
with the proviso that more than 5 mol % of the radicals $R^1$ and/or $R^2$ are present in the polycondensate of the formula I, where $R^1$ is a compound of the formula II or $R^2$ is a compound of the formula III, or $R^1$ is a compound of the formula II and $R^2$ is a compound of the formula III, or in which more than 5 mol % of the radicals $R^1$ and $R^2$ are present in the polycondensate of the formula I, where a) $R^1$ is a compound of the formula V and $R^2$ is a compound of the formula VI, or;

b) $R^1$ is phenyl-1,2; phenyl-1,3 or phenyl-1,4 and $R^2$ is a compound of the formula VI, and with the further proviso that when $R^1$ is a compound of the formula II and both $R^5$ and $R^6$ in formula II are hydrogen, X together with $R^2$ in formula I is not —NH— together with $C^6$-alkyl or —NH— together with xylylene.

12. The composition of claim 11 wherein said polycondensate is 2',3'-(1',4'-diethyl)-L-tartryl poly-(2,3-O-isopropylidene)-L-tartrate.

13. The composition of claim 11 wherein said polycondensate is 2',3'-O-isopropylidene-L-threityl poly-(2,3-O-isopropylidene-L-tartrate.

14. The composition of claim 11 wherein said polycondensate is 2',3'-(1',4'-di-isopropyl)-L-tartryl poly-(2,3,-O-isopropylidene)-L-tartrate.

15. The composition of claim 11 wherein said polycondensate is 2,3-(1,4-diethyl)-L-tartryl polyfurandicarboxylate.

16. The composition of claim 11 wherein said polycondensate is poly-(2,3-(1,4-diethyl)-L-tartryl) terephthalate.

17. The composition of claim 11 wherein said polycondensate is polylysine methylester 2,3,-O-isopropylidene-L-tartramide.

18. A method of for treating an animal or plant organism comprising administering to said organism a controlled release composition of matter comprising a therapeutic agent and a compound comprising:

a polycondensate compound which contains at least 95 mol % of recurring structural units of the formula I

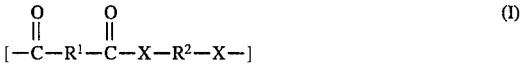

where $R^1$ is
a) straight-chain or branched ($C_1$–$C_{18}$)-alkyl or straight-chain or branched ($C_1$–$C_{18}$)-alkenyl which contains one or more double bonds,
b) straight-chain or branched ($C_1$–$C_{18}$)-alkyl or straight-chain or branched ($C_1$–$C_{18}$)-alkenyl which contains one or more double bonds, mono- or polysubstituted by
  1) ($C_5$–$C_7$)-cycloalkyl,
  2) ($C_5$–$C_7$)-cycloalkenyl, having one or more double bonds,
  3) halogen,
  4) mercapto,
  5) hydroxy,
  6) ($C_1$–$C_6$)-alkoxy,
  7) phenoxy,
  8) phenoxy, mono- or polysubstituted by
    8.1 halogen,
    8.2 ($C_1$–$C_6$)-alkyl,
    8.3 ($C_1$–$C_6$)-alkoxy,
    8.4 nitro or
    8.5 carbethoxy,
  9) naphthyloxy,
  10) benzyloxy,
  11) benzyloxy, mono- or polysubstituted in the aryl moiety by
    11.1 methoxy,
    11.2 carboxamid,
    11.3 amino,
    11.4 halogen,
    11.5 nitro or
    11.6 methyl,
  12) amino,
  13) monoalkylamino, having 1 to 7 carbon atoms,
  14) monoalkylamino, having 1 to 7 carbon atoms, mono- or polysubstituted in the alkyl moiety by
    14.1 hydroxyl,
    14.2 carboxyl,
    14.3 carboxamide,
    14.4 carboethoxy,
    14.5 amino,
    14.6 ($C_1$–$C_6$)-alkylamino,
    14.7 di-($C_1$–$C_6$)-alkylamino,
    14.8 piperidine or
    14.9 morpholine,
  15) dialkylamino having 1 to 7 carbon atoms, or
  16) dialkylamino having 1 to 7 carbon atoms, substituted as defined in b) 14.1 to 14.9, c) aryl, having 6 to 14 carbon atoms, optionally mono- or disubstituted by
- 1.1 $(C_1-C_6)$-alkyl,
- 1.2 $(C_2-C_6)$-alkenyl,
- 1.3 $(C_1-C_6)$ alkylcarboxy,
- 1.4 hydroxyl,
- 1.5 halogen,
- 1.6 acetoxy,
- 1.7 $(C_1-C_6)$-alkylcarboxamide,
- 1.8 sulfonamide,
- 1.9 nitro,
- 1.10 $(C_1-C_6)$-alkoxy or
- 1.11 amino, d) a compound of the formula IV

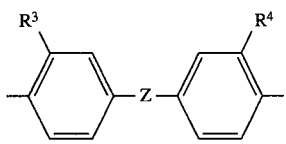 (IV)

in which $R^3$ and $R^4$ independently of one another are
1) hydrogen or
2) an inert radical and wherein Z is a compound
1) —O—,
2) —S—,
3) ,
4) —SO$_2$—
5) ,
6) —C$_n$H$_{2n}$—, in which n is an integer from 1 to 10 and the carbon chain is straight or branched, or
7) —O-aryl-O, in which aryl is as defined in c), e) a compound of the formula II,

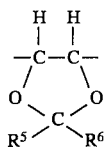 (II)

in which $R^5$ and $R^6$ independently of one another are
1) hydrogen,
2) alkyl or alkenyl having 1 to 18 carbon atoms,
3) alkyl or alkenyl having 1 to 18 carbon atoms, mono- or polysubstituted as defined in b) 1 to 16,
4) aryl, having 6 to 14 carbon atoms,
5) aryl, having 6 to 14 carbon atoms, mono- or polysubstituted as defined in c) 1.1 to 1.11, or f) a compound of the formula V

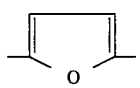 (V)

where X in formula I is
a) —O—,
b) —NH— or
c) —S—, where $R^2$ in formula I is
a) a compound of the formula III

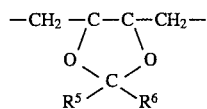 (III)

in which $R^5$ and $R^6$ have the above-mentioned meanings, b) a compound of the formula VI,

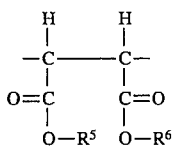 (VI)

in which $R^5$ and $R^6$ have the above-mentioned meanings, c) straight-chain or branched alkyl or alkenyl having 1 to 18 carbon atoms, d) straight-chain or branched alkyl or alkenyl having 1 to 18 carbon atoms, mono- or polysubstituted by a radical wherein said radical is
1) carboxyl,
2) carboxyl in which the hydroxyl group is replaced by a radical wherein said radical is
  - 2.1 —O-$(C_1-C_8)$-alkyl,
  - 2.2 halogen,
  - 2.3 —O-$(C_1-C_4)$-alkylcarbonyl,
  - 2.4 $(C_1-C_6)$-alkylamino,
  - 2.5 $(C_1-C_6)$-alkylamino, mono- or polysubstituted in the alkyl moiety by a radical wherein said radical is
    - 2.5.1 hydroxyl,
    - 2.5.2 mercapto,
    - 2.5.3 —O-$(C_2-C_4)$-alkyl,
  - 2.6 L-amino acid or genetically encoded L-amino acid,
  - 2.7 L-amino acid or genetically encoded L-amino acid, either of which is mono- or polysubstituted by
    - 2.7.1 $(C_1-C_4)$-alkyl
3) hydroxyl,
4) halogen,
5) amino,
6) mercapto or
7) alkyl having 1 to 8 carbon atoms, e) a cyclic compound of the formula VII

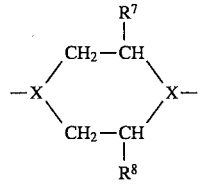 (VII)

in which $R^7$ and $R^8$, independently of one another, are
1) hydrogen or
2) $(C_1-C_3)$-alkyl
and X is N, or f) aryl, having 5 to 14 carbon atoms, optionally mono- or disubstituted by
- 1.1 $(C_1-C_6)$-alkyl,
- 1.2 $(C_2-C_6)$-alkenyl,
- 1.3 $(C_1-C_6)$-alkylcarboxy, 1.4 hydroxyl,
1.5 halogen,
1.6 acetoxy,
1.7 $(C_1-C_6)$-alkylcarboxamide,
1.8 sulfonamide,
1.9 nitro,
1.10 $(C_1-C_6)$-alkoxy or
1.11 amino, with the proviso that more than 5 mol % of the radicals $R^1$ and/or $R^2$ are present in the polycondensate of the formula I, where $R^1$ is a compound of the formula II or is a compound $R^2$ is a compound of the formula III, or $R^1$ is a compound of the formula II and $R^2$ is a compound of the formula III, or in which more than 5 mol % of the radicals $R_1$ and $R^2$ are present in the polycondensate of the formula I, where a) $R^1$ is a compound of the formula V and $R^2$ is a compound of the formula VI, or;

b) $R^1$ is phenyl-1,2; phenyl-1,3 or phenyl-1,4 and $R^2$ is a compound of the formula VI, and with the further proviso that when $R^1$ is a compound of the formula II and both $R^5$ and $R^6$ in formula II are hydrogen, X together with $R^2$ in formula I is not —NH— together with $C_6$-alkyl or —NH— together with xylylene.

19. The method of claim 18 wherein said polycondensate is 2',3'-(1',4'-diethyl)-L-tartryl poly-(2,3-O-isopropylidene)-L-tartrate.

20. The method of claim 18 wherein said polycondensate is 2',3'-O-isopropylidene-L-threityl poly-(2,3-O-isopropylidene-L-tartrate.

21. The method of claim 18 wherein said polycondensate is 2',3'-(1',4'-di-isopropyl)-L-tartryl poly-(2,3,-O-isopropylidene)-L-tartrate.

22. The method of claim 18 wherein said polycondensate is 2,3-(1,4-diethyl)-L-tartryl polyfurandicarboxylate.

23. The method of claim 18 wherein said polycondensate is poly-(2,3-(1,4-diethyl)-L-tartryl) terephthalate.

24. The method of claim 18 wherein said polycondensate is polylysine methylester 2,3, -O-isopropylidene-L-tartramide.

25. The method of according to claim 18 where said organism comprises an animal organism.

26. The method according to any one of claims 18 to 24 where said organism comprises a mammalian organism.

27. The method according to any one of claims 18 to 24 where said organism comprises a mammalian organism and said therapeutic agent comprises buserelin.

* * * * *

UNITED STATES PATENT AND TRADEMARK OFFICE
CERTIFICATE OF CORRECTION

PATENT NO. : 5,505,784
DATED : April 09, 1996
INVENTOR(S) : Volker KRONE et al

It is certified that error appears in the above-indentified patent and that said Letters Patent is hereby corrected as shown below:

Claim 1, Column 18, Line 20, "R1" should read --$R^1$--;
Line 21, "R5 and R6" should read --$R^5$ and $R^6$--;
Line 22, "R2" should read --$R^2$--;
Line 23, "C6-alkyl" should read --$C_6$-alkyl--.

Claim 11, Column 21, Line 61, "$C^6$-alkyl" should read --$C_6$-alkyl--.

Claim 18, Column 25, Line 15, "$R_1$" should read --$R^1$--.

Signed and Sealed this

Third Day of September, 1996

Attest:

BRUCE LEHMAN

*Attesting Officer*    *Commissioner of Patents and Trademarks*